United States Patent
Lu et al.

(10) Patent No.: US 7,574,251 B2
(45) Date of Patent: Aug. 11, 2009

(54) METHOD AND SYSTEM FOR ADAPTING A RADIATION THERAPY TREATMENT PLAN BASED ON A BIOLOGICAL MODEL

(75) Inventors: Weiguo Lu, Madison, WI (US); Kenneth J. Ruchala, Madison, WI (US); Gustavo H. Olivera, Madison, WI (US); Eric Schnarr, McFarland, WI (US); Jeffrey M. Kapatoes, Madison, WI (US); Thomas R. Mackie, Verona, WI (US); Paul J. Reckwerdt, Madison, WI (US)

(73) Assignee: TomoTherapy Incorporated, Madison, WI (US)

( * ) Notice: Subject to any disclaimer, the term of this patent is extended or adjusted under 35 U.S.C. 154(b) by 21 days.

(21) Appl. No.: 11/459,105

(22) Filed: Jul. 21, 2006

(65) Prior Publication Data

US 2007/0043286 A1    Feb. 22, 2007

Related U.S. Application Data

(60) Provisional application No. 60/701,580, filed on Jul. 22, 2005.

(51) Int. Cl.
*A61B 5/05* (2006.01)
(52) U.S. Cl. .................................. 600/427; 600/411
(58) Field of Classification Search ................ 600/315, 600/407, 427; 378/65, 901
See application file for complete search history.

(56) References Cited

U.S. PATENT DOCUMENTS

| | | | |
|---|---|---|---|
| 3,949,265 A | 4/1976 | Holl | |
| 3,964,467 A | 6/1976 | Rose | |
| 4,006,422 A | 2/1977 | Schriber | |
| 4,032,810 A | 6/1977 | Eastham et al. | |
| 4,149,081 A | 4/1979 | Seppi | |
| 4,181,894 A | 1/1980 | Pottier | |
| 4,189,470 A | 2/1980 | Rose | |
| 4,208,185 A | 6/1980 | Sawai et al. | |
| 4,273,867 A | 6/1981 | Lin et al. | |
| 4,314,180 A | 2/1982 | Salisbury | |
| 4,335,465 A | 6/1982 | Christiansen et al. | |

(Continued)

FOREIGN PATENT DOCUMENTS

CA     2091275     9/1993

(Continued)

OTHER PUBLICATIONS

PCT/US06/28553 International Search Report and Written Opinion mailed Sep. 20, 2007.

(Continued)

*Primary Examiner*—Eric F Winakur
*Assistant Examiner*—Michael T Rozanski
(74) *Attorney, Agent, or Firm*—Michael Best & Friedrich LLP (57) ABSTRACT

A system and method of adapting a radiation therapy treatment plan. The method includes the acts of preparing a treatment plan for a patient, acquiring images of the patient, performing deformable registration of the images, acquiring data relating to a radiation dose delivered to the patient, applying a biological model relating the radiation dose delivered and a patient effect, and adapting the radiation therapy treatment plan based on the deformable registration and the biological model.

18 Claims, 5 Drawing Sheets

U.S. PATENT DOCUMENTS

| | | |
|---|---|---|
| 4,388,560 A | 6/1983 | Robinson et al. |
| 4,393,334 A | 7/1983 | Glaser |
| 4,395,631 A | 7/1983 | Salisbury |
| 4,401,765 A | 8/1983 | Craig et al. |
| 4,426,582 A | 1/1984 | Orloff et al. |
| 4,446,403 A | 5/1984 | Cuomo et al. |
| 4,480,042 A | 10/1984 | Craig et al. |
| 4,570,103 A | 2/1986 | Schoen |
| 4,664,869 A | 5/1987 | Mirzadeh et al. |
| 4,703,018 A | 10/1987 | Craig et al. |
| 4,715,056 A | 12/1987 | Vlasbloem et al. |
| 4,736,106 A | 4/1988 | Kashy et al. |
| 4,752,692 A | 6/1988 | Jergenson et al. |
| 4,754,760 A | 7/1988 | Fukukita et al. |
| 4,815,446 A | 3/1989 | McIntosh |
| 4,818,914 A | 4/1989 | Brodie |
| 4,868,844 A | 9/1989 | Nunan |
| 4,870,287 A | 9/1989 | Cole et al. |
| 4,879,518 A | 11/1989 | Broadhurst |
| 4,912,731 A | 3/1990 | Nardi |
| 4,936,308 A | 6/1990 | Fukukita et al. |
| 4,987,309 A | 1/1991 | Klasen et al. |
| 4,998,268 A | 3/1991 | Winter |
| 5,003,998 A | 4/1991 | Collett |
| 5,008,907 A | 4/1991 | Norman et al. |
| 5,012,111 A | 4/1991 | Ueda |
| 5,065,315 A | 11/1991 | Garcia |
| 5,073,913 A | 12/1991 | Martin |
| 5,084,682 A | 1/1992 | Swenson et al. |
| 5,107,222 A | 4/1992 | Tsuzuki |
| 5,124,658 A | 6/1992 | Adler |
| 5,210,414 A | 5/1993 | Wallace et al. |
| 5,250,388 A | 10/1993 | Schoch et al. |
| 5,317,616 A | 5/1994 | Swerdloff et al. |
| 5,335,255 A | 8/1994 | Seppi et al. |
| 5,346,548 A | 9/1994 | Mehta |
| 5,351,280 A | 9/1994 | Swerdloff et al. |
| 5,382,914 A | 1/1995 | Hamm et al. |
| 5,391,139 A | 2/1995 | Edmundson |
| 5,394,452 A | 2/1995 | Swerdloff et al. |
| 5,405,309 A | 4/1995 | Carden |
| 5,442,675 A | 8/1995 | Swerdloff et al. |
| 5,453,310 A | 9/1995 | Andersen et al. |
| 5,466,587 A | 11/1995 | Fitzpatrick-McElligott et al. |
| 5,471,516 A | 11/1995 | Nunan |
| 5,483,122 A | 1/1996 | Derbenev et al. |
| 5,489,780 A | 2/1996 | Diamondis |
| 5,523,578 A | 6/1996 | Herskovic |
| 5,528,650 A | 6/1996 | Swerdloff et al. |
| 5,548,627 A | 8/1996 | Swerdloff et al. |
| 5,576,602 A | 11/1996 | Hiramoto et al. |
| 5,578,909 A | 11/1996 | Billen |
| 5,581,156 A | 12/1996 | Roberts et al. |
| 5,596,619 A | 1/1997 | Carol |
| 5,596,653 A | 1/1997 | Kurokawa |
| 5,621,779 A | 4/1997 | Hughes et al. |
| 5,622,187 A | 4/1997 | Carol |
| 5,625,663 A | 4/1997 | Swerdloff et al. |
| 5,627,041 A | 5/1997 | Shartle |
| 5,641,584 A | 6/1997 | Andersen et al. |
| 5,647,663 A | 7/1997 | Holmes |
| 5,651,043 A | 7/1997 | Tsuyuki et al. |
| 5,661,377 A | 8/1997 | Mishin et al. |
| 5,661,773 A | 8/1997 | Swerdloff et al. |
| 5,667,803 A | 9/1997 | Paronen et al. |
| 5,668,371 A | 9/1997 | Deasy et al. |
| 5,673,300 A | 9/1997 | Reckwerdt et al. |
| 5,692,507 A | 12/1997 | Seppi et al. |
| 5,695,443 A | 12/1997 | Brent et al. |
| 5,712,482 A | 1/1998 | Gaiser et al. |
| 5,721,123 A * | 2/1998 | Hayes et al. ............... 435/91.1 |
| 5,724,400 A | 3/1998 | Swerdloff et al. |
| 5,729,028 A | 3/1998 | Rose |
| 5,734,168 A | 3/1998 | Yao |
| 5,747,254 A | 5/1998 | Pontius |
| 5,751,781 A | 5/1998 | Brown et al. |
| 5,753,308 A | 5/1998 | Andersen et al. |
| 5,754,622 A | 5/1998 | Hughes |
| 5,754,623 A | 5/1998 | Seki |
| 5,760,395 A | 6/1998 | Johnstone |
| 5,802,136 A | 9/1998 | Carol |
| 5,811,944 A | 9/1998 | Sampayan et al. |
| 5,815,547 A | 9/1998 | Shepherd et al. |
| 5,818,058 A | 10/1998 | Nakanishi et al. |
| 5,818,902 A | 10/1998 | Yu |
| 5,820,553 A | 10/1998 | Hughes |
| 5,821,051 A | 10/1998 | Androphy et al. |
| 5,821,705 A | 10/1998 | Caporaso et al. |
| 5,834,454 A | 11/1998 | Kitano et al. |
| 5,836,905 A | 11/1998 | Lemelson et al. |
| 5,842,175 A | 11/1998 | Andros et al. |
| 5,866,912 A | 2/1999 | Slater et al. |
| 5,870,447 A | 2/1999 | Powell et al. |
| 5,877,023 A | 3/1999 | Sautter et al. |
| 5,877,192 A | 3/1999 | Lindberg et al. |
| 5,912,134 A | 6/1999 | Shartle |
| 5,920,601 A | 7/1999 | Nigg et al. |
| 5,953,461 A | 9/1999 | Yamada |
| 5,962,995 A | 10/1999 | Avnery |
| 5,963,615 A | 10/1999 | Egley et al. |
| 5,969,367 A | 10/1999 | Hiramoto et al. |
| 5,977,100 A | 11/1999 | Kitano et al. |
| 5,983,424 A | 11/1999 | Naslund |
| 5,986,274 A | 11/1999 | Akiyama et al. |
| 6,011,825 A | 1/2000 | Welch et al. |
| 6,020,135 A | 2/2000 | Levine et al. |
| 6,020,538 A | 2/2000 | Han et al. |
| 6,029,079 A | 2/2000 | Cox et al. |
| 6,038,283 A | 3/2000 | Carol et al. |
| 6,049,587 A | 4/2000 | Leksell et al. |
| 6,066,927 A | 5/2000 | Koudijs |
| 6,069,459 A | 5/2000 | Koudijs |
| 6,071,748 A | 6/2000 | Modlin et al. |
| 6,094,760 A | 8/2000 | Nonaka et al. |
| 6,127,688 A | 10/2000 | Wu |
| 6,152,599 A | 11/2000 | Salter |
| 6,171,798 B1 | 1/2001 | Levine et al. |
| 6,178,345 B1 | 1/2001 | Vilsmeier et al. |
| 6,197,328 B1 | 3/2001 | Yanagawa |
| 6,198,957 B1 | 3/2001 | Green |
| 6,200,959 B1 | 3/2001 | Haynes et al. |
| 6,204,510 B1 | 3/2001 | Ohkawa |
| 6,207,400 B1 | 3/2001 | Kwon |
| 6,218,675 B1 | 4/2001 | Akiyama et al. |
| 6,222,905 B1 | 4/2001 | Yoda et al. |
| 6,241,670 B1 | 6/2001 | Nambu |
| 6,242,747 B1 | 6/2001 | Sugitani et al. |
| 6,264,825 B1 | 7/2001 | Blackburn et al. |
| 6,265,837 B1 | 7/2001 | Akiyama et al. |
| 6,279,579 B1 | 8/2001 | Riaziat et al. |
| 6,291,823 B1 | 9/2001 | Doyle et al. |
| 6,316,776 B1 | 11/2001 | Hiramoto et al. |
| 6,319,469 B1 | 11/2001 | Mian et al. |
| 6,322,249 B1 | 11/2001 | Wofford et al. |
| 6,331,194 B1 | 12/2001 | Elizondo-Decanini et al. |
| 6,345,114 B1 | 2/2002 | Mackie et al. |
| 6,360,116 B1 | 3/2002 | Jackson, Jr. et al. |
| 6,385,286 B1 | 5/2002 | Fitchard et al. |
| 6,385,288 B1 | 5/2002 | Kanematsu |
| 6,393,096 B1 | 5/2002 | Carol et al. |
| 6,405,072 B1 | 6/2002 | Cosman |
| 6,407,505 B1 | 6/2002 | Bertsche |
| 6,417,178 B1 | 7/2002 | Klunk et al. |
| 6,424,856 B1 | 7/2002 | Vilsmeier et al. |

| | | | | | | |
|---|---|---|---|---|---|---|
| 6,428,547 B1 | 8/2002 | Vilsmeier et al. | 6,889,695 B2 | 5/2005 | Pankratov et al. | |
| 6,433,349 B2 | 8/2002 | Akiyama et al. | 6,922,455 B2 | 7/2005 | Jurczyk et al. | |
| 6,438,202 B1 | 8/2002 | Olivera et al. | 6,929,398 B2 | 8/2005 | Tybinkowski et al. | |
| 6,455,844 B1 | 9/2002 | Meyer | 6,936,832 B2 | 8/2005 | Norimine et al. | |
| 6,462,490 B1 | 10/2002 | Matsuda et al. | 6,955,464 B1 | 10/2005 | Tybinkowski et al. | |
| 6,465,957 B1 | 10/2002 | Whitham et al. | 6,963,171 B2 | 11/2005 | Sagawa et al. | |
| 6,466,644 B1 | 10/2002 | Hughes et al. | 6,974,254 B2 | 12/2005 | Paliwal et al. | |
| 6,469,058 B1 | 10/2002 | Grove et al. | 6,984,835 B2 | 1/2006 | Harada | |
| 6,472,834 B2 | 10/2002 | Hiramoto et al. | 6,990,167 B2 | 1/2006 | Chen | |
| 6,473,490 B1 | 10/2002 | Siochi | 7,015,490 B2 | 3/2006 | Wang et al. | |
| 6,475,994 B2 | 11/2002 | Tomalia et al. | 7,046,762 B2 * | 5/2006 | Lee | 378/65 |
| 6,482,604 B2 | 11/2002 | Kwon | 7,051,605 B2 | 5/2006 | Lagraff et al. | |
| 6,484,144 B2 | 11/2002 | Martin et al. | 7,060,997 B2 | 6/2006 | Norimine et al. | |
| 6,487,274 B2 | 11/2002 | Bertsche | 7,077,569 B1 | 7/2006 | Tybinkowski et al. | |
| 6,493,424 B2 | 12/2002 | Whitham | 7,081,619 B2 | 7/2006 | Bashkirov et al. | |
| 6,497,358 B1 | 12/2002 | Walsh | 7,084,410 B2 | 8/2006 | Beloussov et al. | |
| 6,498,011 B2 | 12/2002 | Hohn et al. | 7,087,200 B2 | 8/2006 | Taboas et al. | |
| 6,500,343 B2 | 12/2002 | Siddiqi | 7,112,924 B2 | 9/2006 | Hanna | |
| 6,504,899 B2 | 1/2003 | Pugachev et al. | 7,130,372 B2 | 10/2006 | Kusch et al. | |
| 6,510,199 B1 | 1/2003 | Hughes et al. | 7,154,991 B2 | 12/2006 | Earnst et al. | |
| 6,512,942 B1 | 1/2003 | Burdette et al. | 7,186,986 B2 | 3/2007 | Hinderer et al. | |
| 6,516,046 B1 | 2/2003 | Frohlich et al. | 7,186,991 B2 | 3/2007 | Kato et al. | |
| 6,527,443 B1 | 3/2003 | Vilsmeier et al. | 7,203,272 B2 | 4/2007 | Chen | |
| 6,531,449 B2 | 3/2003 | Khojasteh et al. | 7,209,547 B2 | 4/2007 | Baier et al. | |
| 6,535,837 B1 | 3/2003 | Schach Von Wittenau | 7,221,733 B1 | 5/2007 | Takai et al. | |
| 6,552,338 B1 | 4/2003 | Doyle | 7,252,307 B2 | 8/2007 | Kanbe et al. | |
| 6,558,961 B1 | 5/2003 | Sarphie et al. | 7,257,196 B2 | 8/2007 | Brown et al. | |
| 6,560,311 B1 | 5/2003 | Shepard et al. | 2002/0007918 A1 | 1/2002 | Owen et al. | |
| 6,562,376 B2 | 5/2003 | Hooper et al. | 2002/0077545 A1 | 6/2002 | Takahashi et al. | |
| 6,584,174 B2 | 6/2003 | Schubert et al. | 2002/0080915 A1 | 6/2002 | Frohlich | |
| 6,586,409 B1 | 7/2003 | Wheeler | 2002/0085668 A1 | 7/2002 | Blumhofer et al. | |
| 6,605,297 B2 | 8/2003 | Nadachi et al. | 2002/0091314 A1 | 7/2002 | Schlossbauer et al. | |
| 6,611,700 B1 | 8/2003 | Vilsmeier et al. | 2002/0115923 A1 | 8/2002 | Erbel | |
| 6,617,768 B1 | 9/2003 | Hansen | 2002/0120986 A1 | 9/2002 | Erbel et al. | |
| 6,618,467 B1 | 9/2003 | Ruchala et al. | 2002/0122530 A1 | 9/2002 | Erbel et al. | |
| 6,621,889 B1 | 9/2003 | Mostafavi | 2002/0136439 A1 | 9/2002 | Ruchala et al. | |
| 6,633,686 B1 | 10/2003 | Bakircioglu et al. | 2002/0150207 A1 | 10/2002 | Kapatoes et al. | |
| 6,634,790 B1 | 10/2003 | Salter, Jr. | 2002/0187502 A1 | 12/2002 | Waterman et al. | |
| 6,636,622 B2 | 10/2003 | Mackie et al. | 2002/0193685 A1 | 12/2002 | Mate et al. | |
| 6,637,056 B1 | 10/2003 | Tybinkowski et al. | 2003/0007601 A1 | 1/2003 | Jaffray et al. | |
| 6,646,383 B2 | 11/2003 | Bertsche et al. | 2003/0031298 A1 | 2/2003 | Xing | |
| 6,653,547 B2 | 11/2003 | Akamatsu | 2003/0086527 A1 | 5/2003 | Speiser et al. | |
| 6,661,870 B2 | 12/2003 | Kapatoes et al. | 2003/0105650 A1 | 6/2003 | Lombardo et al. | |
| 6,688,187 B1 | 2/2004 | Masquelier | 2003/0174872 A1 | 9/2003 | Chalana et al. | |
| 6,690,965 B1 | 2/2004 | Riaziat et al. | 2004/0010418 A1 | 1/2004 | Buonocore et al. | |
| 6,697,452 B2 | 2/2004 | Xing | 2004/0068182 A1 | 4/2004 | Misra | |
| 6,705,984 B1 | 3/2004 | Angha | 2004/0116804 A1 | 6/2004 | Mostafavi | |
| 6,713,668 B2 | 3/2004 | Akamatsu | 2004/0165696 A1 | 8/2004 | Lee | |
| 6,713,976 B1 | 3/2004 | Zumoto et al. | 2004/0202280 A1 | 10/2004 | Besson | |
| 6,714,620 B2 | 3/2004 | Caflisch et al. | 2004/0230115 A1 | 11/2004 | Scarantino et al. | |
| 6,714,629 B2 | 3/2004 | Vilsmeier | 2004/0254492 A1 | 12/2004 | Zhang et al. | |
| 6,716,162 B2 | 4/2004 | Hakamata | 2004/0254773 A1 | 12/2004 | Zhang et al. | |
| 6,723,334 B1 | 4/2004 | McGee et al. | 2004/0264640 A1 | 12/2004 | Myles | |
| 6,760,402 B2 | 7/2004 | Ghelmansarai | 2005/0013406 A1 | 1/2005 | Dyk et al. | |
| 6,774,383 B2 | 8/2004 | Norimine et al. | 2005/0031181 A1 | 2/2005 | Bi et al. | |
| 6,787,771 B2 | 9/2004 | Garty et al. | 2005/0080332 A1 | 4/2005 | Shiu et al. | |
| 6,787,983 B2 | 9/2004 | Yamanobe et al. | 2005/0096515 A1 * | 5/2005 | Geng | 600/315 |
| 6,788,764 B2 | 9/2004 | Saladin et al. | 2005/0123092 A1 | 6/2005 | Mistretta et al. | |
| 6,792,073 B2 | 9/2004 | Deasy et al. | 2005/0143965 A1 | 6/2005 | Failla et al. | |
| 6,796,164 B2 | 9/2004 | McLoughlin et al. | 2005/0180544 A1 | 8/2005 | Sauer et al. | |
| 6,800,866 B2 | 10/2004 | Amemiya et al. | 2005/0197564 A1 | 9/2005 | Dempsey | |
| 6,822,244 B2 | 11/2004 | Beloussov et al. | 2005/0251029 A1 | 11/2005 | Khamene et al. | |
| 6,822,247 B2 | 11/2004 | Sasaki | 2006/0074292 A1 * | 4/2006 | Thomson et al. | 600/411 |
| 6,838,676 B1 | 1/2005 | Jackson | 2006/0083349 A1 | 4/2006 | Harari et al. | |
| 6,842,502 B2 | 1/2005 | Jaffray et al. | 2006/0100738 A1 | 5/2006 | Alsafadi et al. | |
| 6,844,689 B1 | 1/2005 | Brown et al. | 2006/0133568 A1 | 6/2006 | Moore | |
| 6,871,171 B1 | 3/2005 | Agur et al. | 2006/0193429 A1 | 8/2006 | Chen | |
| 6,873,115 B2 | 3/2005 | Sagawa et al. | 2006/0193441 A1 | 8/2006 | Cadman | |
| 6,873,123 B2 | 3/2005 | Marchand et al. | 2006/0285639 A1 | 12/2006 | Olivera et al. | |
| 6,878,951 B2 | 4/2005 | Ma | 2007/0041494 A1 | 2/2007 | Ruchala et al. | |
| 6,882,702 B2 | 4/2005 | Luo | 2007/0041495 A1 | 2/2007 | Olivera et al. | |
| 6,882,705 B2 | 4/2005 | Egley et al. | 2007/0041497 A1 | 2/2007 | Schnarr et al. | |
| 6,888,326 B2 | 5/2005 | Amaldi et al. | | | | |

| | | | |
|---|---|---|---|
| 2007/0041498 | A1 | 2/2007 | Olivera et al. |
| 2007/0041499 | A1 | 2/2007 | Lu et al. |
| 2007/0041500 | A1 | 2/2007 | Olivera et al. |
| 2007/0076846 | A1 | 4/2007 | Ruchala et al. |
| 2007/0088573 | A1 | 4/2007 | Ruchala et al. |
| 2007/0104316 | A1 | 5/2007 | Ruchala et al. |
| 2007/0127623 | A1 | 6/2007 | Goldman et al. |
| 2007/0189591 | A1 | 8/2007 | Lu et al. |
| 2007/0195922 | A1 | 8/2007 | Mackie et al. |
| 2007/0195929 | A1 | 8/2007 | Ruchala et al. |
| 2007/0195930 | A1 | 8/2007 | Kapatoes et al. |
| 2007/0201613 | A1 | 8/2007 | Lu et al. |
| 2007/0211857 | A1 | 9/2007 | Urano et al. |

FOREIGN PATENT DOCUMENTS

| | | |
|---|---|---|
| CA | 2180227 | 12/1996 |
| WO | WO 03/076003 | 9/2003 |
| WO | 2004057515 | 7/2004 |

OTHER PUBLICATIONS

Karen Miller, "The Phantom Torso", RT Image, vol. 14 No. 25, Jun. 18, 2001.

Ronald D. Rogus et al., "Accuracy of a Photogrammetry-Based Patient Positioning and Monitoring System for Radiation Therapy," Medical Physics, vol. 26, Issue 5, May 1999.

D. Rueckert et al., "Nonrigid Registration Using Free-Form Deformations: Application to Breast MR Images," IEEE Transactions on Medical Imaging, vol. 18, No. 8, Aug. 1999.

Yuan-Nan Young, "Registration-Based Morphing of Active Contours for Segmentation of CT Scans," Mathematical Biosciences and Engineering, vol. 2, No. 1, Jan. 2005.

Anthony Yezzi et al., "A Variational Framework for Joint Segmentation and Registration," Mathematical Method in Biomedical Image Analysis, 2001. (Note: the title of the periodical and the date listed are from the International Search Report, however they do not appear on the article itself.).

* cited by examiner

METHOD AND SYSTEM FOR ADAPTING A RADIATION THERAPY TREATMENT PLAN BASED ON A BIOLOGICAL MODEL

RELATED APPLICATIONS

This application claims priority to U.S. Provisional Patent Application No. 60/701,580, filed on Jul. 22, 2005, titled SYSTEM AND METHOD FOR FEEDBACK GUIDED QUALITY ASSURANCE AND ADAPTATIONS TO RADIATION THERAPY TREATMENT, the entire contents of which are incorporated herein by reference.

BACKGROUND

Over the past decades improvements in computers and networking, radiation therapy treatment planning software, and medical imaging modalities (CT, MRI, US, and PET) have been incorporated into radiation therapy practice. These improvements have led to the development of image guided radiation therapy ("IGRT"). IGRT is radiation therapy that uses cross-sectional images of the patient's internal anatomy to better target the radiation dose in the tumor while reducing the radiation exposure to healthy organs. The radiation dose delivered to the tumor is controlled with intensity modulated radiation therapy ("IMRT"), which involves changing the size, shape, and intensity of the radiation beam to conform to the size, shape, and location of the patient's tumor. IGRT and IMRT lead to improved control of the tumor while simultaneously reducing the potential for acute side effects due to irradiation of healthy tissue surrounding the tumor.

IMRT is becoming the standard of care in several countries. However, in many situations, IMRT is not used to treat a patient due to time, resources, and billing constraints. Daily images of the patient can be used to guarantee that the high gradients generated by IMRT plans are located on the correct position for patient treatment. Also these images can provide necessary information to adapt the plan online or offline if needed.

It is commonly known in the field of radiation therapy that there are many sources of uncertainty and change that can occur during a course of a patient's treatment. Some of these sources represent random errors, such as small differences in a patient's setup position each day. Other sources are attributable to physiological changes, which might occur if a patient's tumor regresses or the patient loses weight during therapy. A third possible category regards motion. Motion can potentially overlap with either of the other categories, as some motion might be more random and unpredictable, such as a patient coughing or passing gas, whereas other motion can be more regular, such as breathing motion, sometimes.

SUMMARY

In radiation therapy, uncertainties can affect the quality of a patient's treatment. For example, when delivering a treatment dose to a target region, it is standard practice to also treat a high-dose "margin" region about the target. This helps ensure that the target receives the desired dose, even if its location changes during the course of the treatment, or even during a single fraction. The less definite a target's location, the larger the margins that typically need to be used.

Adaptive radiation therapy generally refers to the concept of using feedback during the course of radiation therapy treatment to improve future treatments. Feedback can be used in off-line adaptive therapy processes and on-line adaptive therapy processes. Off-line adaptive therapy processes occur while the patient is not being treated, such as in between treatment fractions. In one version of this, during each fraction, a new CT image of the patient is acquired before or after each of the fractions. After the images are acquired from the first few treatment fractions, the images are evaluated to determine an effective envelope of the multi-day locations of target structures. A new plan can then be developed to better reflect the range of motion of the target structure, rather than using canonical assumptions of motion. A more complex version of off-line adaptive therapy is to recalculate the delivered dose after each fraction and accumulate these doses, potentially utilizing deformation techniques, during this accumulation to account for internal motion. The accumulated dose can then be compared to the planned dose, and if any discrepancies are noted, subsequent fractions can be modified to account for the changes.

On-line adaptive therapy processes typically occur while the patient is in the treatment room, and potentially, but not necessarily, during a treatment delivery. For example, some radiation therapy treatment systems are equipped with imaging systems, such as on-line CT or x-ray systems. These systems can be used prior to treatment to validate or adjust the patient's setup for the treatment delivery. The imaging systems may also be used to adapt the treatment during the actual treatment delivery. For example, an imaging system potentially can be used concurrently with treatment to modify the treatment delivery to reflect changes in patient anatomy.

One aspect of the present invention is to disclose new opportunities for the application of adaptive therapy techniques, and additional aspects are to present novel methods for adaptive therapy. In particular, adaptive therapy has typically focused on feedback to modify a patient's treatment, but the present invention focuses on adaptive therapy processes being used in a quality assurance context. This is particularly true in the context of whole-system verification.

For example, a detector can be used to collect information indicating how much treatment beam has passed through the patient, from which the magnitude of the treatment output can be determined as well as any radiation pattern that was used for the delivery. The benefit of this delivery verification process is that it enables the operator to detect errors in the machine delivery, such as an incorrect leaf pattern or machine output.

However, validating that the machine is functioning properly does not itself ensure proper delivery of a treatment plan, as one also needs to validate that the external inputs used to program the machine are effective and consistent. Thus, one aspect of the invention includes the broader concept of an adaptive-type feedback loop for improved quality assurance of the entire treatment process. In this aspect, the invention includes the steps of positioning the patient for treatment and using a method for image-guidance to determine the patient's position, repositioning the patient as necessary for treatment based upon the image-guidance, and beginning treatment. Then, either during or after treatment, recalculating the patient dose and incorporating the patient image information that had been collected before or during treatment. After completion of these steps, quality assurance data is collected to analyze the extent to which the delivery was not only performed as planned, but to validate that the planned delivery is reasonable in the context of the newly available data. In this regard, the concept of feedback is no longer being used to indicate changes to the treatment based on changes in the patient or delivery, but to validate the original delivery itself.

As an example, it is possible that a treatment plan might be developed for a patient, but that the image used for planning became corrupted, such as by applying an incorrect density calibration. In this case, the treatment plan will be based upon incorrect information, and might not deliver the correct dose to the patient. Yet, many quality assurance techniques will not detect this error because they will verify that the machine is operating as instructed, rather than checking whether the instructions to the machine are based on correct input information. Likewise, some adaptive therapy techniques could be applied to this delivery, but if the calibration problem of this example persisted, then the adapted treatments would suffer from similar flaws.

There are a number of processes that can be used to expand the use of feedback for quality assurance purposes. For example, in one embodiment, this process would include the delivery verification techniques described above. The validation of machine performance that these methods provide is a valuable component of a total-system quality assurance toolset. Moreover, the delivery verification processes can be expanded to analyze other system errors, such as deliveries based on images with a truncated field-of-view.

In one embodiment, the invention provides a method of adapting a treatment plan. The method includes the acts of preparing a treatment plan for a patient, acquiring images of the patient, performing deformable registration of the images, acquiring data relating to a radiation dose delivered to the patient, applying a biological model to relate the radiation dose delivered and a patient effect, and adapting the treatment plan based on the deformable registration and the biological model.

In another embodiment, the invention provides a method of delivering radiation therapy to a patient. The method includes the acts of acquiring an on-line image of at least a portion of the patient while the patient is in a first position, calculating a predictive radiation dose to be delivered to the patient, and applying a biological model to determine a biological effect of the predictive radiation dose on the patient in the first position.

In yet another embodiment, the invention provides a computer program embodied by a computer readable medium capable of being executed by a computer, the computer program for use in a treatment system. The computer program comprises a treatment plan module operable to generate a treatment plan for a patient, an image acquisition module operable to acquire images of at least a portion of the patient, a deformation module operable to generate a deformable registration between at least two of the images, and a modeling module operable to relate a radiation dose delivered to the patient and an effect of the radiation dose on the patient and to adapt the treatment plan based on the deformable registration and the biological model.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first", "second", and "third" are used herein for purposes of description and are not intended to indicate or imply relative importance or significance.

In addition, it should be understood that embodiments of the invention include both hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Figure 1:
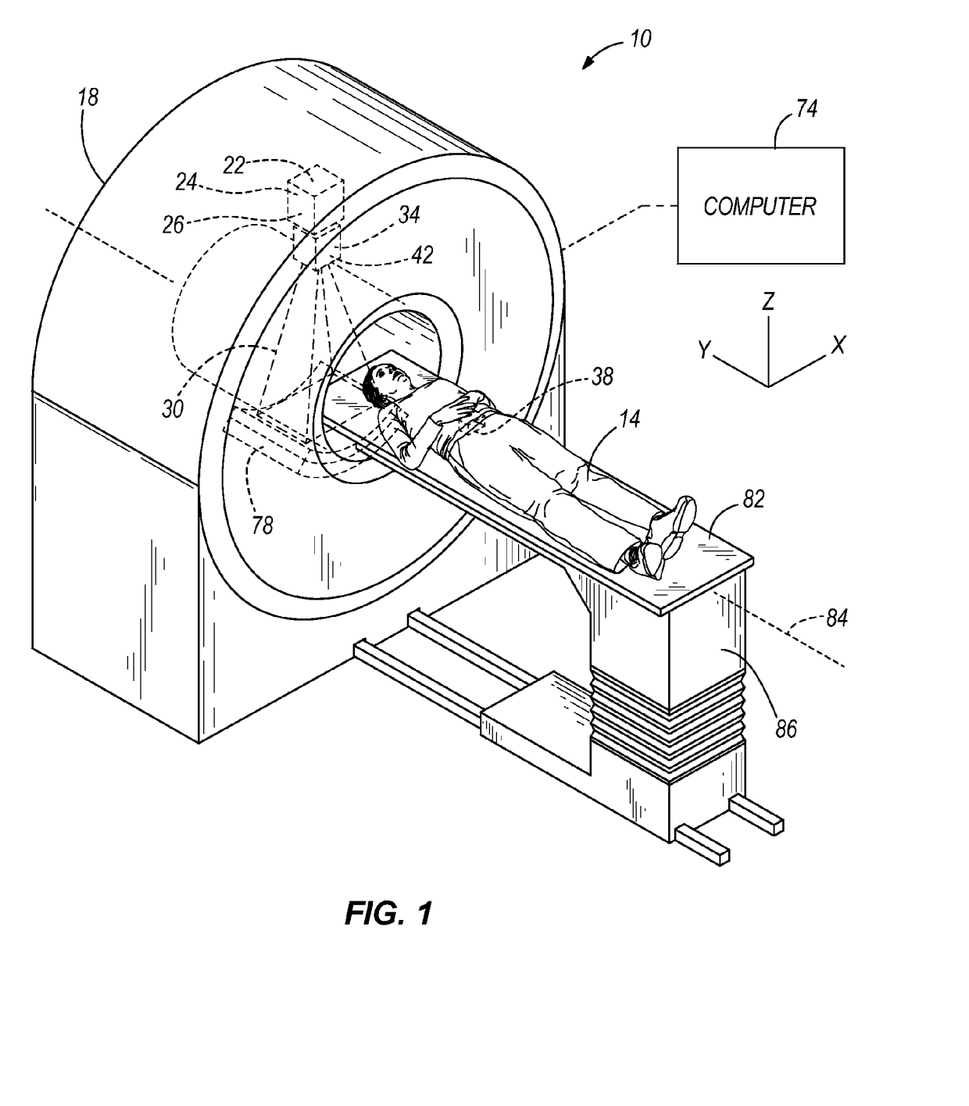
FIG. 1 is a perspective view of a radiation therapy treatment system.

FIG. 1 illustrates a radiation therapy treatment system 10 that can provide radiation therapy to a patient 14. The radiation therapy treatment can include photon-based radiation therapy, brachytherapy, electron beam therapy, proton, neutron, or particle therapy, or other types of treatment therapy. The radiation therapy treatment system 10 includes a gantry 18. The gantry 18 can support a radiation module 22, which can include a radiation source 24 and a linear accelerator 26 operable to generate a beam 30 of radiation. Though the gantry 18 shown in the drawings is a ring gantry, i.e., it extends through a full 360° arc to create a complete ring or circle, other types of mounting arrangements may also be employed. For example, a C-type, partial ring gantry, or robotic arm could be used. Any other framework capable of positioning the radiation module 22 at various rotational and/or axial positions relative to the patient 14 may also be employed. In addition, the radiation source 24 may travel in path that does not follow the shape of the gantry 18. For example, the radiation source 24 may travel in a non-circular path even though the illustrated gantry 18 is generally circular-shaped.

The radiation module 22 can also include a modulation device 34 operable to modify or modulate the radiation beam 30. The modulation device 34 provides the modulation of the radiation beam 30 and directs the radiation beam 30 toward the patient 14. Specifically, the radiation beam 34 is directed toward a portion of the patient. Broadly speaking, the portion may include the entire body, but is generally smaller than the entire body and can be defined by a two-dimensional area and/or a three-dimensional volume. A portion desired to receive the radiation, which may be referred to as a target 38 or target region, is an example of a region of interest. The target 38 may also include a margin around or partially around the target. Another type of region of interest is a region at risk. If a portion includes a region at risk, the radiation beam is preferably diverted from the region at risk. The patient 14 may have more than one target region that needs to receive radiation therapy. Such modulation is sometimes referred to as intensity modulated radiation therapy ("IMRT").

Figure 2:
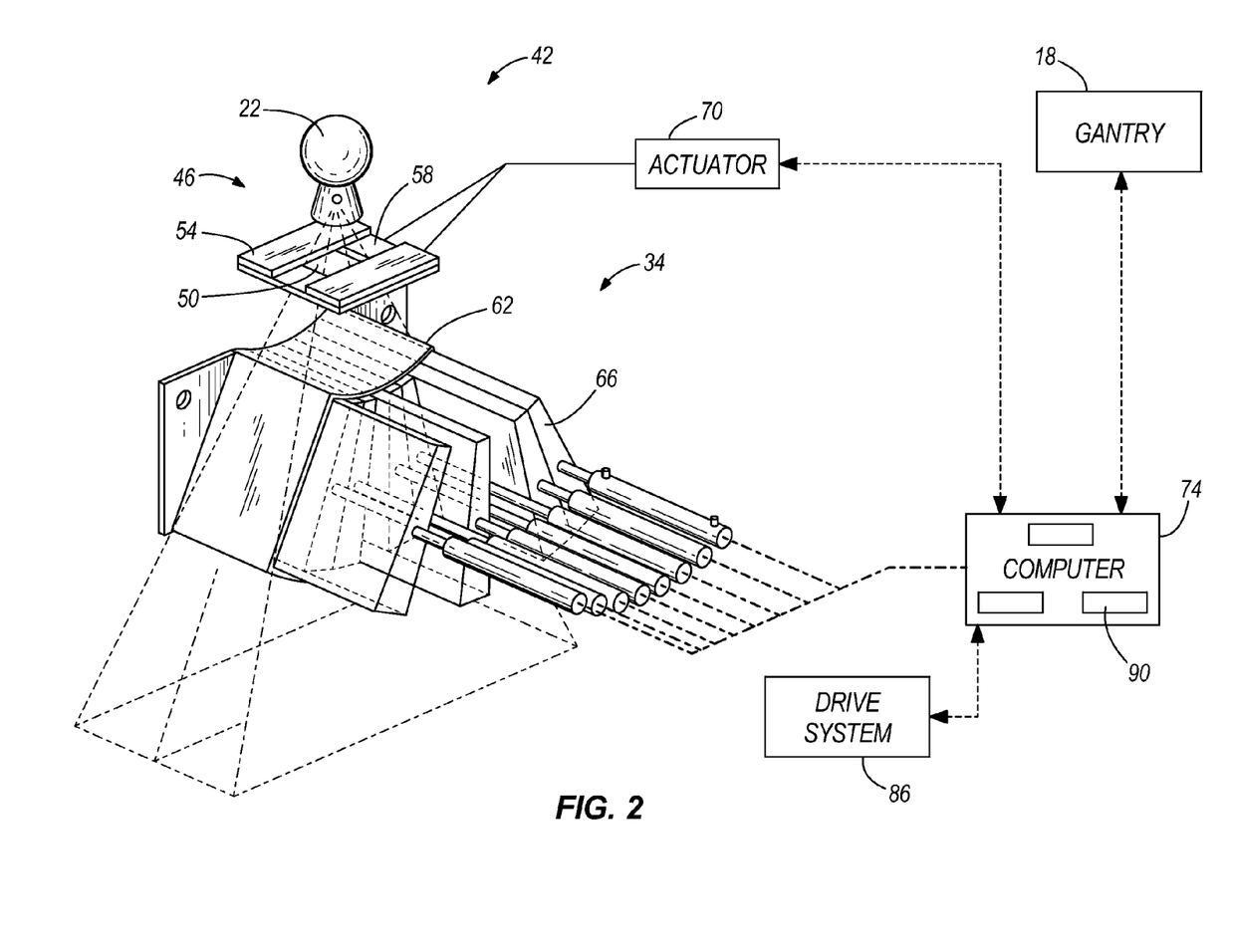
FIG. 2 is a perspective view of a multi-leaf collimator that can be used in the radiation therapy treatment system illustrated in FIG. 1.

The modulation device 34 can include a collimation device 42 as illustrated in FIG. 2. The collimation device 42 includes a set of jaws 46 that define and adjust the size of an aperture 50 through which the radiation beam 30 may pass. The jaws 46 include an upper jaw 54 and a lower jaw 58. The upper jaw 54 and the lower jaw 58 are moveable to adjust the size of the aperture 50.

In one embodiment, and illustrated in FIG. 2, the modulation device 34 can comprise a multi-leaf collimator 62, which includes a plurality of interlaced leaves 66 operable to move from position to position, to provide intensity modulation. It is also noted that the leaves 66 can be moved to a position anywhere between a minimally and maximally-open position. The plurality of interlaced leaves 66 modulate the strength, size, and shape of the radiation beam 30 before the radiation beam 30 reaches the target 38 on the patient 14. Each of the leaves 66 is independently controlled by an actuator 70, such as a motor or an air valve so that the leaf 66 can open and close quickly to permit or block the passage of radiation. The actuators 70 can be controlled by a computer 74 and/or controller.

The radiation therapy treatment system 10 can also include a detector 78, e.g., a kilovoltage or a megavoltage detector, operable to receive the radiation beam 30. The linear accelerator 26 and the detector 78 can also operate as a computed tomography (CT) system to generate CT images of the patient 14. The linear accelerator 26 emits the radiation beam 30 toward the target 38 in the patient 14. The target 38 absorbs some of the radiation. The detector 78 detects or measures the amount of radiation absorbed by the target 38. The detector 78 collects the absorption data from different angles as the linear accelerator 26 rotates around and emits radiation toward the patient 14. The collected absorption data is transmitted to the computer 74 to process the absorption data and to generate images of the patient's body tissues and organs. The images can also illustrate bone, soft tissues, and blood vessels.

The CT images can be acquired with a radiation beam 30 that has a fan-shaped geometry, a multi-slice geometry or a cone-beam geometry. In addition, the CT images can be acquired with the linear accelerator 26 delivering megavoltage energies or kilovoltage energies. It is also noted that the acquired CT images can be registered with previously acquired CT images (from the radiation therapy treatment system 10 or other image acquisition devices, such as other CT scanners, MRI systems, and PET systems). For example, the previously acquired CT images for the patient 14 can include identified targets 38 made through a contouring process. The newly acquired CT images for the patient 14 can be registered with the previously acquired CT images to assist in identifying the targets 38 in the new CT images. The registration process can use rigid or deformable registration tools.

In some embodiments, the radiation therapy treatment system 10 can include an x-ray source and a CT image detector. The x-ray source and the CT image detector operate in a similar manner as the linear accelerator 26 and the detector 78 as described above to acquire image data. The image data is transmitted to the computer 74 where it is processed to generate images of the patient's body tissues and organs.

The radiation therapy treatment system 10 can also include a patient support, such as a couch 82 (illustrated in FIG. 1), which supports the patient 14. The couch 82 moves along at least one axis 84 in the x, y, or z directions. In other embodiments of the invention, the patient support can be a device that is adapted to support any portion of the patient's body. The patient support is not limited to having to support the entire patient's body. The system 10 also can include a drive system 86 operable to manipulate the position of the couch 82. The drive system 86 can be controlled by the computer 74.

Figure 3:
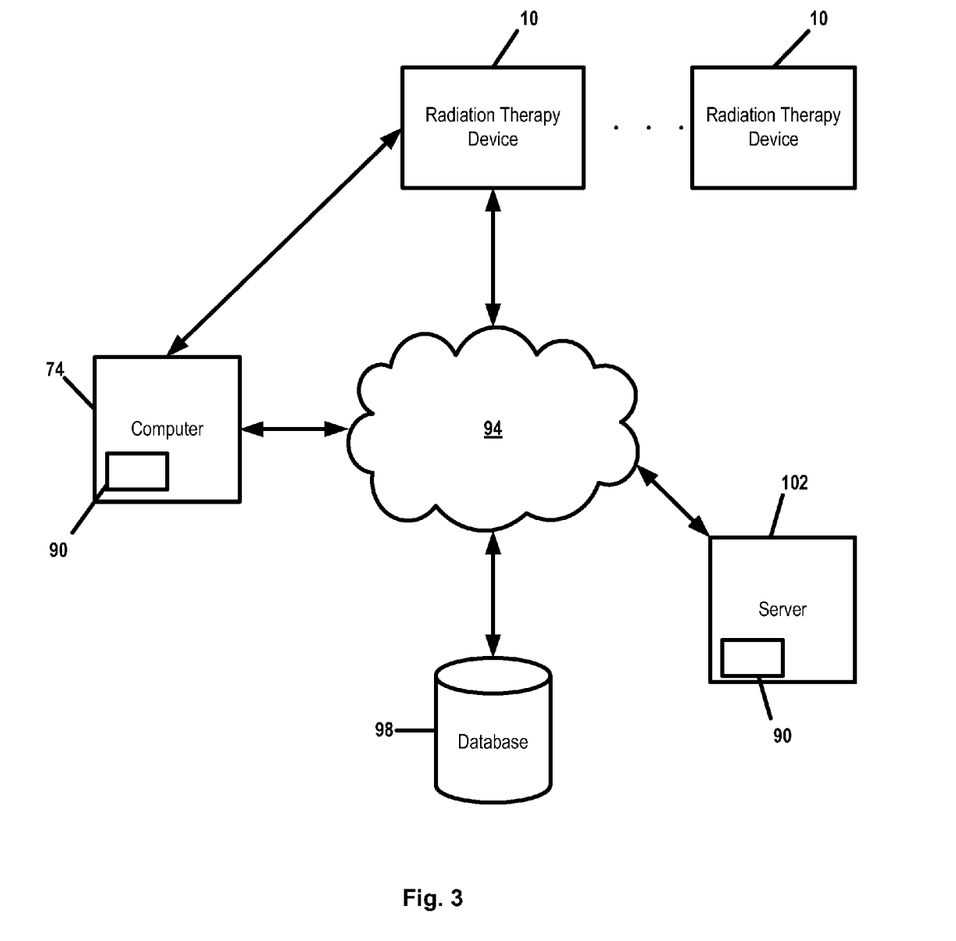
FIG. 3 is a schematic illustration of the radiation therapy treatment system of FIG. 1.

The computer 74, illustrated in FIGS. 2 and 3, includes an operating system for running various software programs and/or a communications application. In particular, the computer 74 can include a software program(s) 90 that operates to communicate with the radiation therapy treatment system 10. The software program(s) 90 is operable to receive data from external software programs and hardware and it is noted that data may be input to the software program(s) 90.

The computer 74 can include any suitable input/output device adapted to be accessed by medical personnel. The computer 74 can include typical hardware such as a processor, I/O interfaces, and storage devices or memory. The computer 74 can also include input devices such as a keyboard and a mouse. The computer 74 can further include standard output devices, such as a monitor. In addition, the computer 74 can include peripherals, such as a printer and a scanner.

The computer 74 can be networked with other computers 74 and radiation therapy treatment systems 10. The other computers 74 may include additional and/or different computer programs and software and are not required to be identical to the computer 74, described herein. The computers 74 and radiation therapy treatment system 10 can communicate with a network 94. The computers 74 and radiation therapy treatment systems 10 can also communicate with a database(s) 98 and a server(s) 102. It is noted that the software program(s) 90 could also reside on the server(s) 102.

The network 94 can be built according to any networking technology or topology or combinations of technologies and topologies and can include multiple sub-networks. Connections between the computers and systems shown in FIG. 3 can be made through local area networks ("LANs"), wide area networks ("WANs"), public switched telephone networks ("PSTNs"), wireless networks, Intranets, the Internet, or any other suitable networks. In a hospital or medical care facility, communication between the computers and systems shown in FIG. 3 can be made through the Health Level Seven ("HL7") protocol or other protocols with any version and/or other required protocol. HL7 is a standard protocol which specifies the implementation of interfaces between two computer applications (sender and receiver) from different vendors for electronic data exchange in health care environments. HL7 can allow health care institutions to exchange key sets of data from different application systems. Specifically, HL7 can define the data to be exchanged, the timing of the interchange, and the communication of errors to the application. The formats are generally generic in nature and can be configured to meet the needs of the applications involved.

Communication between the computers and systems shown in FIG. 3 can also occur through the Digital Imaging and Communications in Medicine ("DICOM") protocol with any version and/or other required protocol. DICOM is an international communications standard developed by NEMA that defines the format used to transfer medical image-related data between different pieces of medical equipment. DICOM RT refers to the standards that are specific to radiation therapy data.

The two-way arrows in FIG. 3 generally represent two-way communication and information transfer between the network 94 and any one of the computers 74 and the systems 10 shown in FIG. 3. However, for some medical and computerized equipment, only one-way communication and information transfer may be necessary.

Figure 4:
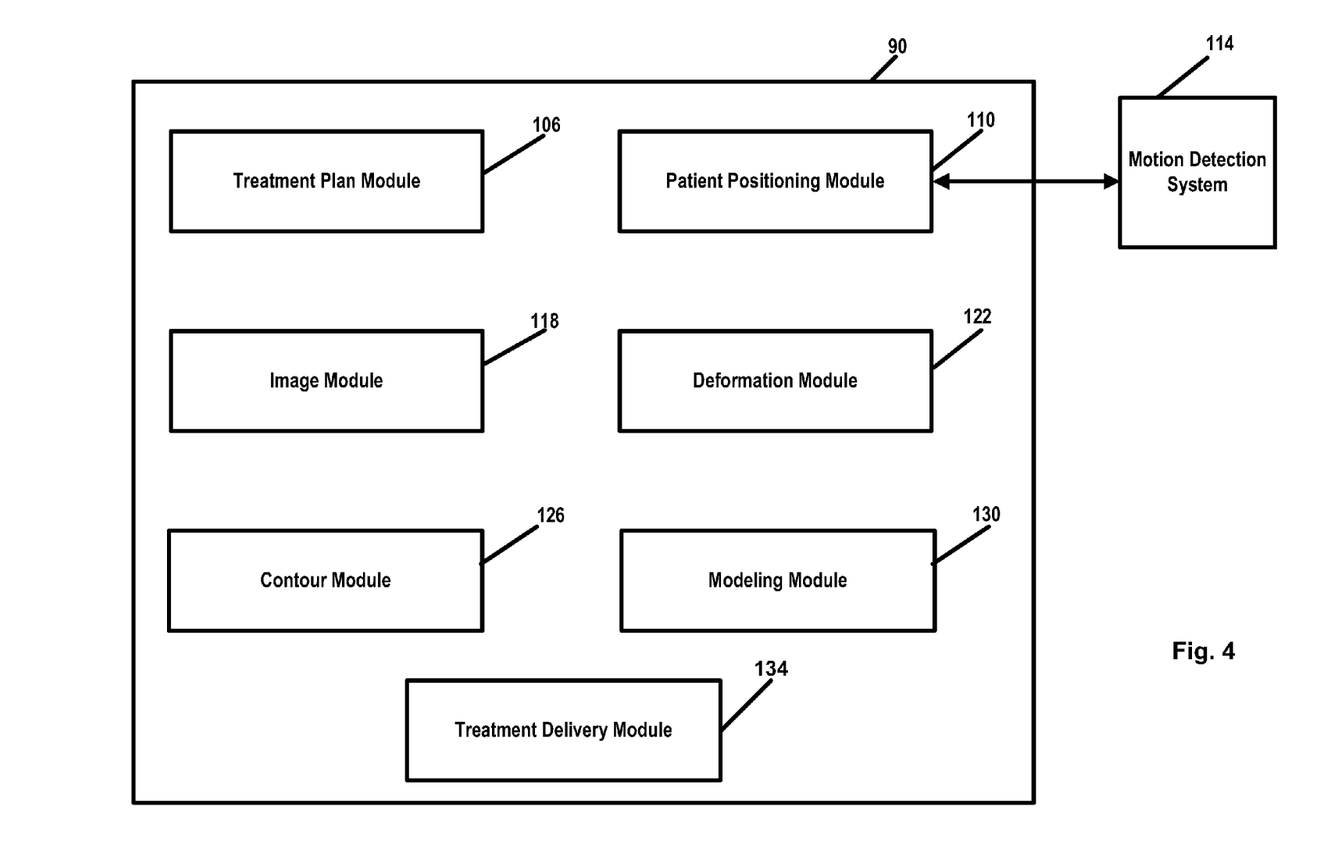
FIG. 4 is a schematic diagram of a software program used in the radiation therapy treatment system.

FIG. 4 is a schematic illustration of the software program 90. The software program 90 includes a plurality of modules that communicate with one another to perform functions of the radiation therapy treatment process.

The software program 90 includes a treatment plan module 106 operable to generate a treatment plan for the patient 14 based on data input to the system 10 by medical personnel. The data includes one or more images (e.g., planning images and/or pre-treatment images) of at least a portion of the patient 14. The treatment plan module 106 separates the treatment into a plurality of fractions and determines the radiation dose for each fraction or treatment based on the prescription input by medical personnel. The treatment plan module 106 also determines the radiation dose for the target 38 based on various contours drawn around the target 38. Multiple targets 38 may be present and included in the same treatment plan.

The software program 90 also includes a patient positioning module 110 operable to position and align the patient 14 with respect to the isocenter of the gantry 18 for a particular treatment fraction. While the patient is on the couch 82, the patient positioning module 110 acquires an image of the patient 14 and compares the current position of the patient 14 to the position of the patient in a planning or previously acquired image. If the patient's position needs to be adjusted, the patient positioning module 110 provides instructions to the drive system 86 to move the couch 82 or the patient 14 can be manually moved to the new position.

In one aspect, the patient positioning module 110 can receive data from lasers positioned in the treatment room to provide patient position data with respect to the isocenter of the gantry 18. Based on the data from the lasers, the patient positioning module 110 provides instructions to the drive system 86, which moves the couch 82 to achieve proper alignment of the patient 14 with respect to the gantry 18. It is noted that devices and systems, other than lasers, can be used to provide data to the patient positioning module 110 to assist in the alignment process.

The patient positioning module 110 also is operable to detect and/or monitor patient motion during treatment. The patient positioning module 110 may communicate with and/or incorporate a motion detection system 114, such as x-ray, in-room CT, laser positioning devices, camera systems, spirometers, ultrasound, tensile measurements, chest bands, and the like. The patient motion can be irregular or unexpected, and does not need to follow a smooth or reproducible path.

The software program 90 also includes an image module 118 operable to acquire images of at least a portion of the patient 14. The image module 118 can instruct the on-board image device, such as a CT imaging device to acquire images of the patient 14 before treatment commences, during treatment, and after treatment according to desired protocols. In one aspect, the image module 118 acquires an image of the patient 14 while the patient 14 is substantially in a treatment position. Other off-line imaging devices or systems may be used to acquire pre-treatment images of the patient 14, such as non-quantitative CT, MRI, PET, SPECT, ultrasound, transmission imaging, fluoroscopy, RF-based localization, and the like. The acquired pre-treatment image(s) can be used for registration of the patient 14 and/or to generate a deformation map to identify the differences between one or more of the planning images and one or more of the pre-treatment, during-treatment, or after-treatment images.

The acquired images also can be used for registration of the patient 14 and/or to determine or predict a radiation dose to be delivered to the patient 14. The acquired images also can be used to determine a radiation dose that the patient 14 received during prior treatments or fractions. The image module 118 also is operable to acquire images of at least a portion of the patient 14 while the patient is receiving treatment to determine a radiation dose that the patient 14 is receiving in real-time.

The software program 90 also includes a deformation module 122 operable to receive data, such as image data from the image module 118 and the treatment plan module 106 and other patient and system data from the treatment plan module 106 to generate a deformation map of the images. The deformation module 122 can use deformation techniques to determine an accumulation of radiation dose for all delivered treatments.

The deformation module 122 can generate a deformation map to identify the differences between one or more images, e.g., planning images pre-treatment images, during-treatment images, and post-treatment images. For example, a deformation map can be utilized to relate a plurality of images where one image is a planning image that is useful for dose calculation, and another image, such as an on-line image, has qualitative value but has less direct utility for dose calculation. This relationship could then be used to "remap" the more quantitative image to the qualitative shape of the on-line or less quantitative image. The resulting remapped image would be more appropriate than either of the other two images for dose calculation or quantitative applications as it would have the quantitative benefits of the first image, but with the updated anatomical information as contained in the second image. This is useful in a variety of cases, such as where the first image (e.g., a planning image) is a CT image and where the second image lacks quantitative image values (e.g., MRI, PET, SPECT, ultrasound, or non-quantitative CT, etc. images).

The deformation module 122 can correct for geometrical distortion, imperfections, and/or incompleteness in lieu of, or in addition to, quantitative limitations. For example, a current MRI image that represents anatomy well but includes geometric distortion might be remapped to a CT image that is not distorted. Or, multiple images can be used to simultaneously correct for distortion while representing anatomical changes.

The deformation map can be used to calculate radiation dose on patient images acquired after the planning image. It is also useful to accumulate the doses for multiple delivered fractions. The doses can be added based upon the location of the doses in physical space, but another method is to incorporate deformation methods into the process so as to add doses based upon the structures that received the dose, even if the structures have changed location. The deformation module 122 can calculate the doses of radiation that the patient 14 has received from previously delivered fractions.

A deformation map can be generated for purposes of defining a contour around a target 38. The software program 90 can include a contour module 126 operable to generate one or more contours on an image. Generally, medical personnel manually define a contour around a target(s) 38 on a planning image. This process is time consuming. Newly-acquired images (e.g., pre-treatment images) do not have the defined contour(s). It is desirable to generate contours on the new image based upon the old image. A deformation map can be used to assist in the contouring process and can create time savings for the medical personnel while providing quality assurance measures.

The contour can be generated automatically or semi-automatically for a new image (e.g., a pre-treatment image). This process begins with a planning or other baseline patient image that has an initial contour set. When performing either quality assurance or adaptive therapy, it is common to have a new image, for which contours are not yet available. Rather than require medical personnel to manually contour the new image, it can be both faster and more consistent to perform a deformable image registration, and then use the deformation results as the basis for modifying the original contour set to reflect the new patient anatomy. It is generally known that manual contours can suffer from irreproducibilities, whereas automatically-generated contours can potentially be more consistent in applying the principles of an initial contour to the generation of subsequent contours.

A similar family of template-based contouring algorithms has been developed to generate contours for newly-available images, based upon previously-available sets of images and contours. These template-based algorithms might contour a new patient image based upon a previous patient image and contour, or potentially based upon a canonical or atlas patient image and contour. This can be performed for adaptive therapy as a means to accumulate doses in daily images, each with automatic daily contours. It is an aspect of this invention to apply deformation-based contouring or template-based contouring to radiation therapy quality assurance and adaptive therapy. In this aspect, the invention applies these techniques to the particular wealth of image data and types of images that arise during image-guided radiation therapy. Specifically, this includes deformation and template-based contouring of multiple images of the same patient in which contour sets might only exist for one of the images. These multiple images of the patient may arise from use of an on-line or in-room patient imaging system, with images potentially taken on different days, or these images might derive from a "4D" imaging system such as a CT scanner, in which each image represents a phase of motion, such as a breathing phase. It should also be noted that the on-line or in-room imaging system might be the same, a similar, or a different modality from the reference image. For example, the reference image might be a CT image, whereas the on-line image could be CT image, a cone-beam CT image, a megavoltage CT image, a MRI image, an ultrasound image, or an image generated by a different system or device. By porting these contouring techniques to the applications of quality assurance and adaptive therapy, it is possible to both save a considerable amount of time from the contouring of images, and this method can also improve the consistency of contours across multiple images of the same patient (taken at different times or representing different phases).

Another benefit of this process is that the contours generated provide a validation of the deformation process. If the generated contours closely reflect contours that one would manually draw, then it is a good indication that the deformation process is reasonable; whereas if the automatic contours are less relevant, it indicates to the medical personnel that perhaps the deformation is inappropriate, but also provides the medical personnel an opportunity to verify the manual contours to check for mistakes or inconsistencies. Another aspect of this invention is that the deformation-based contours can be used as a rough-draft of the contours for the adaptive process, and manually edited to reflect the desired contours for the on-line images. When doing this, the deformation process can then be re-run, constraining the deformation map to match the initial contours to the manually-edited automatic contours, and this helps direct consistent results through the rest of the image.

While the deformation process above was described in the context of registering one image to another image, it can also work with deformably registering a set of two or more images with another set of one or more images. For example, if there are two pairs of images, each pair comprising an MRI and a CT image, then the deformation map can register the two MRI images together in regions where the MRI has more information, and the CT images together where the CT has more information. These deformations can then be combined. Or deformation maps between the images could be used together, such as for using the CT deformation maps to correct for geometric distortion, imperfections, and/or incompleteness in the MRI images and deformations, and then, having corrected that distortion, imperfections, and/or incompleteness using the MRI deformation maps for better analysis of soft-tissue motion. In a general sense, this process enables imaging improvement via deformation, as poor images can be better understood, and therefore improved, by applying deformation techniques that indicate information like anatomical sizes, shapes, and content. This information can be incorporated into image reconstruction, modification, or enhancement processes.

The software program 90 also includes a modeling module 130 operable to generate and apply a biological model for estimating biological effects for a particular treatment. The biological model can be based upon measurements and models describing the effects of radiation on tissues, tumors, and organs and using knowledge of prescribed or delivered doses. The modeling module 130 can apply a biological model to determine patient effects, and also the effect that the location and/or movement of the patient had on the delivery of the prescribed radiation dose. Based on the biological effects, the medical personnel can adjust the patient 14, the system settings, or make other adjustments in the treatment plan. The biological information can be incorporated in the patient registration process to identify a preferred position for the patient 14 that results in a delivered dose with a preferred biological effect.

The modeling module 130 can utilize data related to the radiation dose actually delivered to the patient and the biological effects of the radiation dose delivered to apply a biological model to relate the radiation dose delivered to the patient and the corresponding patient effects. To relate the radiation dose and the patient effects means a simple comparison or active constraint on a biological model. The net radiation dose delivered (accumulated using deformation techniques) can be used to estimate the biological effect that would result from continuing the treatment, and likewise, possible alternatives for adapting the treatment would be evaluated for a preferred biological effect. The resulting fractionation schedule, dose distribution, and plans can reflect this culmination of information.

The patient or biological effects can be tracked or determined over time by physical observations of the patient 14 and/or with biological tracers. For example, biological tracers can include patient markers and radioactive materials that may be inhaled by and/or injected into the patient 14.

An aspect of this invention is to utilize biological models with the combination of both deformation and adaptive therapy. In particular, when accumulating radiation doses as an aspect of adaptive therapy, it is preferable to use deformation techniques, as these help relate the actual received doses to particular tissues, rather than to physical space. Given this, it is desirable to analyze the doses received based upon the biological effects they cause, rather than purely on physical amount of dose.

A particular extension of biological and deformation based dose accumulation applies to the case of 4D images and 4D dose calculation. "4D" images are a collection of 3D image volumes that each represent a "phase" of a motion pattern, such as breathing. Patient motion and dose calculation on the appropriate portions of a 4D CT (or 4D MRI etc.) image can be enhanced by using biological estimators to evaluate the motion-dependent biological effect, based upon the motion-dependent dose distribution. The modeling module 130 can recalculate dose more accurately on one of the 3D volumes.

The modeling module 130 is operable to receive patient data (real-time and historic), patient images (e.g., the planning images and/or the pre-treatment images), patient position data, anatomical position data, and system or machine data. The modeling module 130 can determine the amount of radiation dose that was delivered to the patient 14 by using data from the motion detection system 114 to identify the phase that the patient was in at any given time, and recalculate the radiation dose for each time in the phase of the 4D CT image that best matches the patient's instantaneous position. Based on a better understanding of the amount of radiation dose that the patient is actually receiving, the medical personnel can make adjustments to the treatment plan, patient position/registration during treatment, dose amount, dose distribution, as well as other parameters and system settings. Dose calculations can also be performed on updated 4D CT images, as well as other types of 4D images, such as 4D PET or 4D MRI, that are acquired before or during treatment.

The process of applying biological models can be performed at the end of the treatment and/or during the course of the treatment such that any discrepancies can be detected and potentially corrected. In one implementation, the total radiation dose delivered (accumulated using deformation) is used to estimate the biological effect to the patient 14 that would result from continuing the treatment, and likewise, possible alternatives for adapting the treatment would be evaluated for a preferred biological effect. The resulting fractionation schedule, dose distribution, and plans can be modified to reflect this culmination of information. Additional information that can be incorporated are ranges, magnitudes, and distributions of motion seen throughout the treatment, or from canonical patient studies. The optimization or adaptation of a treatment plan can be performed to account for the biological effect of this motion, and the plan can be modified to best account for it. Similarly, biologically based adaptive therapy need not rely upon physical dose information, but can also utilize knowledge of chemotherapy agent deliveries, especially using tagged agents that could be imaged with PET, SPECT, or other nuclear medicine equipment. Dose targeting could be defined or modified based upon the other agents delivered, their locations, or based on radioimmunotherapy deliveries or feedback.

This process can be expanded to not only last for the duration of the treatment, but to be a means of tracking patient dose and biological effect over a patient's lifetime. The modeling module 130 can generate a model of radiation dose received over a patient's life, and can incorporate dose history, anticipated biological repair, biological effect, and other parameters. Knowledge of this history can be utilized when designing new radiation therapy treatment plans and other medical plans for the patient 14.

Biological information can also be incorporated for the purposes of patient registration. This method improves upon current registration methods, in which on-line images are used to align the patient based upon the image content, the planned dose distribution, the planning contours, etc. In one embodiment, the method would be to collect an on-line image, auto-contour it (potentially using the deformation-based technique discussed above), perform predictive dose calculation, and then estimate the biological effect for the given patient position. Using this model, registration can then be performed based upon finding the image position that results in a delivered dose that results in the optimal or preferred biological effect.

It is another aspect of this invention to use available a priori knowledge to better or more easily identify structures for purposes of biological estimation. For example, biological models typically require definitions of tissue types or structures in images, since different types of structures may react differently to radiation dose. By performing biological analysis in the context of patient quality assurance and adaptive therapy, it is commonly presumed that there is a planning image and initial contours. Thus, when a new on-line image is collected, structures in this image can be automatically identified as particular biological structures, based not only on the raw image information, but also based upon the processing of this image with regard to the a priori images.

Biological modeling methods can also be applied more directly to dose reconstruction by monitoring changes in biological uptake of agents that respond to dose delivered and/or repair mechanisms. For example, FLT can be used for biological dose reconstruction which can be compared with physical dose reconstruction using biological models.

Adaptive biological therapy can also be used with genetic testing, as genetic testing can potentially identify patients in which metastases are occurring on a cellular level that is not yet detectable to other imaging modalities. Adaptive therapy can be applied to these patients to evaluate where dose has been received, what likely regions for metastases are based upon clinical history and dosimetric evaluation, and then determine a treatment plan that would deliver dose to likely metastatic regions.

Another aspect of this invention is that adaptive therapy can be applied not only based upon the radiation doses received alone, but also on predicted trends in the patient's treatment, clinical results, machine changes, and/or biological markers. For example, if a trend is detected in that a tumor is shrinking, or that a normal tissue structure is gradually migrating, the adaptive planning process could not only account for the current status of the patient and the doses delivered to date, but could also generate plans that reflect anticipated further changes in anatomy. Similarly, when analyzing cumulative dose information during the course of a treatment, the medical personnel could also consider the level of clinical effects and side-effects that the patient is experiencing, either based upon clinical findings or available biological markers or tests. If few side effects are felt, a more aggressive adaptive therapy treatment might be pursued, whereas if more complications are detected, the therapy might be modified to better avoid the affected region. Furthermore, plans can be adapted to compensate for detected changes in the machine, such as variations in output, energy, or calibration.

A variation of this aspect is to perform a radiobiopsy. Early in a treatment, or before radiation treatment fully begins, the patient 14 may receive a fraction with a high dose to a localized region, or potentially a dose only to a localized region. The biological effects on this region can be monitored to determine the nature of that region, such as whether it is tumorous, and what type. An appropriate course of treatment can be determined based upon these results, and the dose already delivered can be incorporated into the planning process.

The software program 90 also includes a treatment delivery module 134 operable to instruct the radiation therapy treatment system 10 to deliver radiation therapy to the patient 14 according to the treatment plan. The treatment delivery module 134 can generate and transmit instructions to the gantry 18, the linear accelerator 26, the modulation device 34, and the couch drive system 86 to deliver radiation to the patient 14. The instructions coordinate the necessary movements of the gantry 18, the modulation device 34, and the couch drive system 86 to deliver the radiation beam 30 to the proper target in the proper amount as specified in the treatment plan.

The treatment delivery module 134 also calculates the appropriate pattern, position, and intensity of the radiation beam 30 to be delivered, to match the prescription as specified by the treatment plan. The pattern of the radiation beam 30 is generated by the modulation device 34, and more particularly by movement of the plurality of leaves in the multi-leaf collimator. The treatment delivery module 134 can utilize canonical, predetermined or template leaf patterns to generate the appropriate pattern for the radiation beam 30 based on the treatment parameters. The treatment delivery module 134 can also include a library of patterns for typical cases that can be accessed in which to compare the present patient data to determine the pattern for the radiation beam 30.

Figure 5:
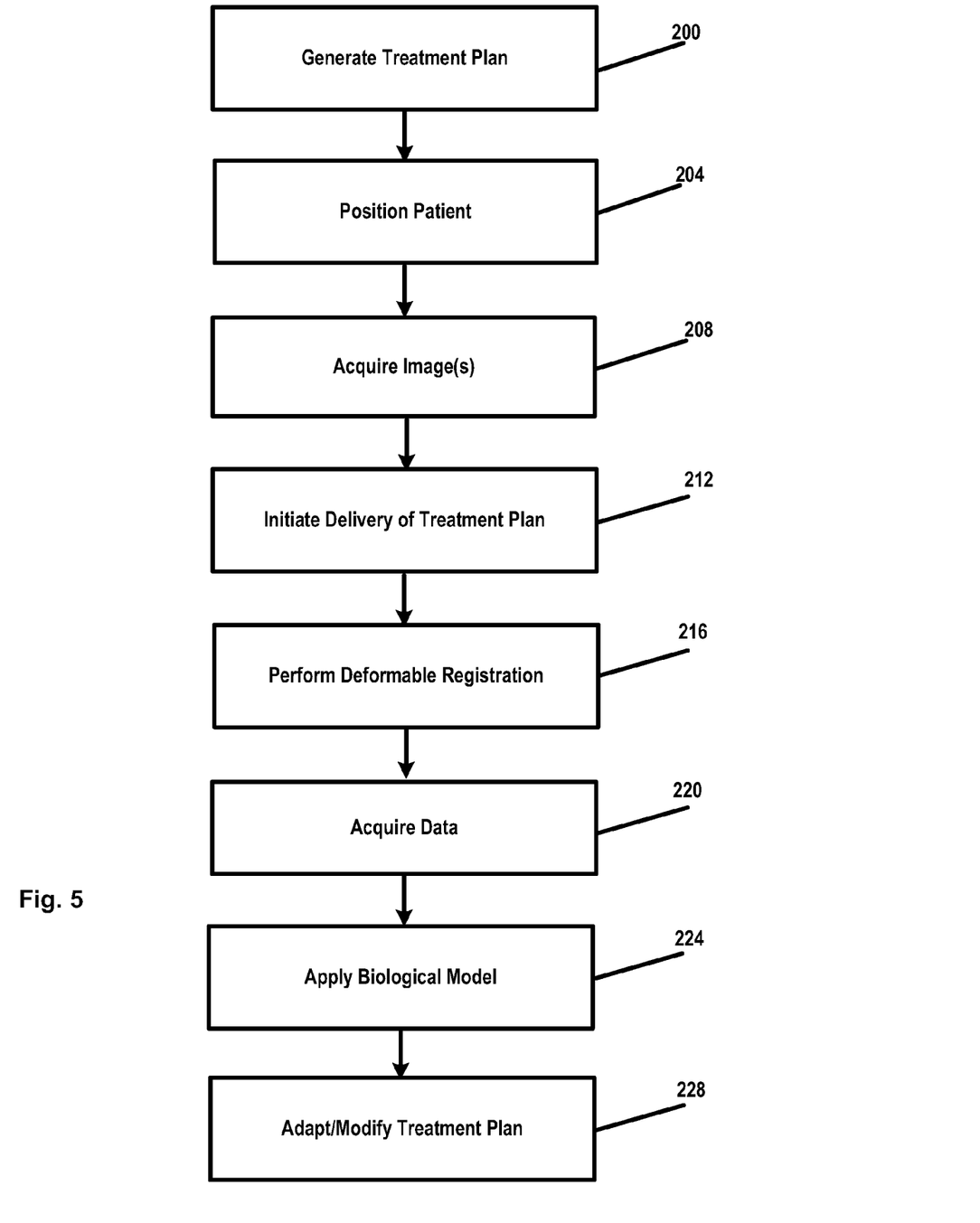
FIG. 5 is a flow chart of a method of evaluating a radiation dose delivered to a patient according to one embodiment of the present invention.

FIG. 5 illustrates a flow chart of a method of adapting a radiation therapy treatment plan according to one embodiment of the invention. Medical personnel generate (at 200) a treatment plan for the patient 14 based on patient data, images, or other information. When the patient 14 is ready for a treatment, medical personnel position (at 204) the patient 14 on the couch 82 with the assistance of the patient positioning module 110 prior to delivery of treatment. Medical personnel initiate (at 208) acquisition of one or more images of the patient 14 while the patient is on the couch 82. After the patient 14 is properly positioned, the medical personnel initiate (at 212) delivery of the treatment plan. Before, during and/or after delivery of the treatment plan, the deformation module 118 performs (at 216) a deformable registration of the one or more images of the patient 14. The modeling module 130 acquires (at 220) data relating to the radiation dose delivered to the patient. The modeling module 130 applies (at 224) a biological model relating the radiation dose delivered and a patient effect. The modeling module 130 also adapts/modifies (at 228) the radiation therapy treatment plan based on the deformable registration and the biological model.

Various features and advantages of the invention are set forth in the following claims.

What is claimed is:

1. A method of adapting a treatment plan, the method comprising:
   preparing a treatment plan for a patient for treating a patient condition, the preparation including acquiring an internal reference image of the patient;
   acquiring three-dimensional internal images of the patient in substantially a treatment position;
   performing deformable registration of the images;
   acquiring data relating to a radiation dose delivered to the patient;
   applying a biological model to relate the radiation dose delivered and a patient effect; and
   adapting subsequent dose delivery of the treatment plan in a radiation delivery device based on the deformable registration and the biological model.

2. A method as set forth in claim 1 wherein the treatment plan is a radiation therapy treatment plan.

3. A method as set forth in claim 1 and further comprising tuning the biological model based on an effect of the radiation dose on the patient.

4. A method as set forth in claim 3 wherein the effect of the radiation dose on the patient can be determined using one of a patient marker and a biological tracer.

5. A method as set forth in claim 1 and further comprising tracking how the patient effect relates to the biological model over a period of time.

6. A method as set forth in claim 5 wherein the period of time is a lifetime of the patient.

7. A method as set forth in claim 5 and further comprising adjusting the biological model parameters based on the relation.

8. A method as set forth in claim 1 and further comprising adapting the treatment plan based on the patient effect.

9. A method as set forth in claim 1 and further comprising evaluating whether a region of interest of the patient moved and wherein the act of adapting the treatment plan incorporates the information relating to motion of the region of interest.

10. A method as set forth in claim 1 and further comprising positioning the patient for a treatment based upon the patient effect of the radiation dose delivered to the patient in prior treatments.

11. A method as set forth in claim 1 and further comprising monitoring the patient effects for trends and adapting the treatment plan based on the trends.

12. A method as set forth in claim 1 wherein the act of adapting the treatment plan further comprises automatically selecting a biological model for evaluation, and automatically applying the biological model to adapt the treatment plan.

13. A method as set forth in claim 1 wherein the biological model is a mathematical model.

14. A method as set forth in claim 1 wherein the biological model is an empirical model.

15. A method as set forth in claim 1 wherein the biological model is a biological effect based on an anatomical influence.

16. A method as set forth in claim 1 wherein the biological model is based on patient metrics.

17. A method as set forth in claim 1 and further comprising performing genetic testing to identify whether the patient condition being treated is predisposed to reoccur.

18. A computer program embodied by a computer readable medium capable of being executed by a computer, the computer program for use in a treatment system, the computer program comprising:
   a treatment plan module operable to generate a treatment plan for a patient, the plan based at least in part on an internal reference image of the patient;
   an image acquisition module operable to acquire a three-dimensional internal image of at least a portion of the patient in substantially a treatment position;
   a deformation module operable to generate a deformable registration between the reference image and the acquired image; and
   a modeling module operable to relate a radiation dose delivered to the patient and an effect of the radiation dose on the patient and to adapt subsequent dose delivery of the treatment plan based on the deformable registration and a biological model.

* * * * *